United States Patent [19]

Hessel

[11] 4,111,204

[45] Sep. 5, 1978

[54] SUCTION COLLECTION SYSTEM

[75] Inventor: Stephen Roy Hessel, Somerville, N.J.

[73] Assignee: C. R. Bard, Inc., Murray Hill, N.J.

[21] Appl. No.: 730,404

[22] Filed: Oct. 7, 1976

[51] Int. Cl.[2] .............................................. A61M 1/00
[52] U.S. Cl. ................................................... 128/276
[58] Field of Search ............................ 128/275–278,
128/2 F; 137/137, 202, 205; 15/351, 353;
73/322.5

[56] References Cited

U.S. PATENT DOCUMENTS

| | | | |
|---|---|---|---|
| 2,730,282 | 1/1956 | Bonner | 226/58 |
| 2,784,717 | 3/1957 | Thompson | 128/276 |
| 3,575,170 | 4/1971 | Clark | 128/275 |
| 3,601,119 | 8/1971 | Engelsher | 128/275 |
| 3,602,223 | 8/1971 | Engelsher | 128/275 |
| 3,683,894 | 8/1972 | Villari | 128/275 |
| 3,704,709 | 12/1972 | Sorenson et al. | 128/277 |
| 3,814,098 | 6/1974 | Deaton | 128/276 |
| 3,982,538 | 9/1976 | Sharpe | 128/276 |
| 3,982,539 | 9/1976 | Muriot | 128/276 |

*Primary Examiner*—Robert W. Michell
*Assistant Examiner*—V. Millin

*Attorney, Agent, or Firm*—Dennison, Dennison, Meserole & Pollack

[57] ABSTRACT

A suction collection system embodying a disposable drainage receiving assembly including a flexible plastic bag sealed to and depending from a lid for positioning within a rigid canister, the open upper end of the canister being sealed by the lid. The lid includes a drainage fixture communicating with the interior of the bag. A suction fixture, also on the lid, communicates with the canister exteriorly of the bag and with the interior of the bag through a restricted fluid path. The suction fixture communication with the canister exteriorly of the bag can be either direct or through a well having a fluid path to the exterior of the bag and a set of apertures opening into the bag. An air pervious-liquid impervious path is orientated solely between the suction fixture and the interior of the bag for an exclusion of liquid and a slight restriction of air flow relative to the flow from the canister exteriorly of the bag. A seal, either a liquid level responsive disc or a compressible tube, will, upon the introduction of a sufficient level of liquid within the bag, terminate communication between the suction fixture and the interior of the bag.

23 Claims, 8 Drawing Figures

SUCTION COLLECTION SYSTEM

The invention herein generally relates to suction collection or drainage systems, and is more particularly concerned with the type of system wherein the actual drainage receiver is a disposable lid-mounted liquid-tight bag selectively positionable in and removable from a permanent rigid canister.

Such collection systems, as evidenced by U.S. Pat. Nos. 3,032,037; 3,719,197; 3,782,384; and 3,814,098, have become increasingly popular as compared to the long used rigid bottles or containers which either constitute an expensive disposable item or give rise to substantial resterilization problems. Known examples of rigid collection systems will be noted in U.S. Pat. Nos. 3,051,175; 3,646,935; 3,699,815; and 3,713,444.

In providing a system or apparatus incorporating a lid-mounted disposable flexible collection bag, several factors must be considered including provision for the suction delivery of body fluids into the sealed bag in a manner whereby spillage and/or contamination of pump equipment and surrounding areas is specifically prevented. Also, in conjunction with the above, care must be taken to avoid any bag collapse or improper suction action therein as the vacuum is drawn and such as could interfere with the collection of the fluid. Other factors to be considered include the ease with which the drainage receiving assembly is to be mounted with the associated surrounding canister, the ease with which the vacuum pump and patient engaging equipment is to be secured to the drainage receiving assembly, and the commercial economics of the system, that is the expense associated with the item which is specifically intended for single-use situations.

The present invention is specifically directed to a suction collection system which effectively and economically provides for the collection and storage of body fluids within a disposable assembly.

The apparatus utilized includes a lid which both mounts the bag, so as to constitute therewith the disposable assembly, and positions the assembly relative to a rigid bag enclosing canister while simultaneously effecting a sealing of the canister.

Provision is also made for a simplified hookup of the collection system, requiring only the connection of a single fluid intake line and a single suction line with the drawing of air through the single suction line attachment effecting both an expansion of the bag through a generation of an initial relatively lower pressure within the canister outside of the bag, and a subsequent suction drawing of fluid through the intake line and into the bag. The pressure differential which provides for an initial expansion of the bag is effected by an air pervious-liquid impervious patch provided within a first fluid path between the suction line and the interior of the bag while a second fluid path between the suction line and the interior of the canister outward of the bag is unencumbered. The patch provides a sufficient resistance to air flow so as to effect the initial drawing of the greater vacuum within the canister. The patch also provides the significant function of precluding the passage of body fluid into the suction line such as could give rise to substantial contamination problems. Finally, an additional sealing is effected by a fluid level responsive disc mounted within the bag below the first fluid path in a manner so as to rise into sealing engagement therewith upon the level of the fluid in the bag rising to a sufficient height. Alternatively, the suction attachment can be provided with a tube portion collapsible in response to a final expansion of the bag.

Additional objects, features and advantages reside in the details of construction and operation of the system as more fully hereinafter described and claimed. Reference is had to the accompanying drawings forming a part hereof wherein like numerals refer to like parts throughout, and in which:

Figure 1:
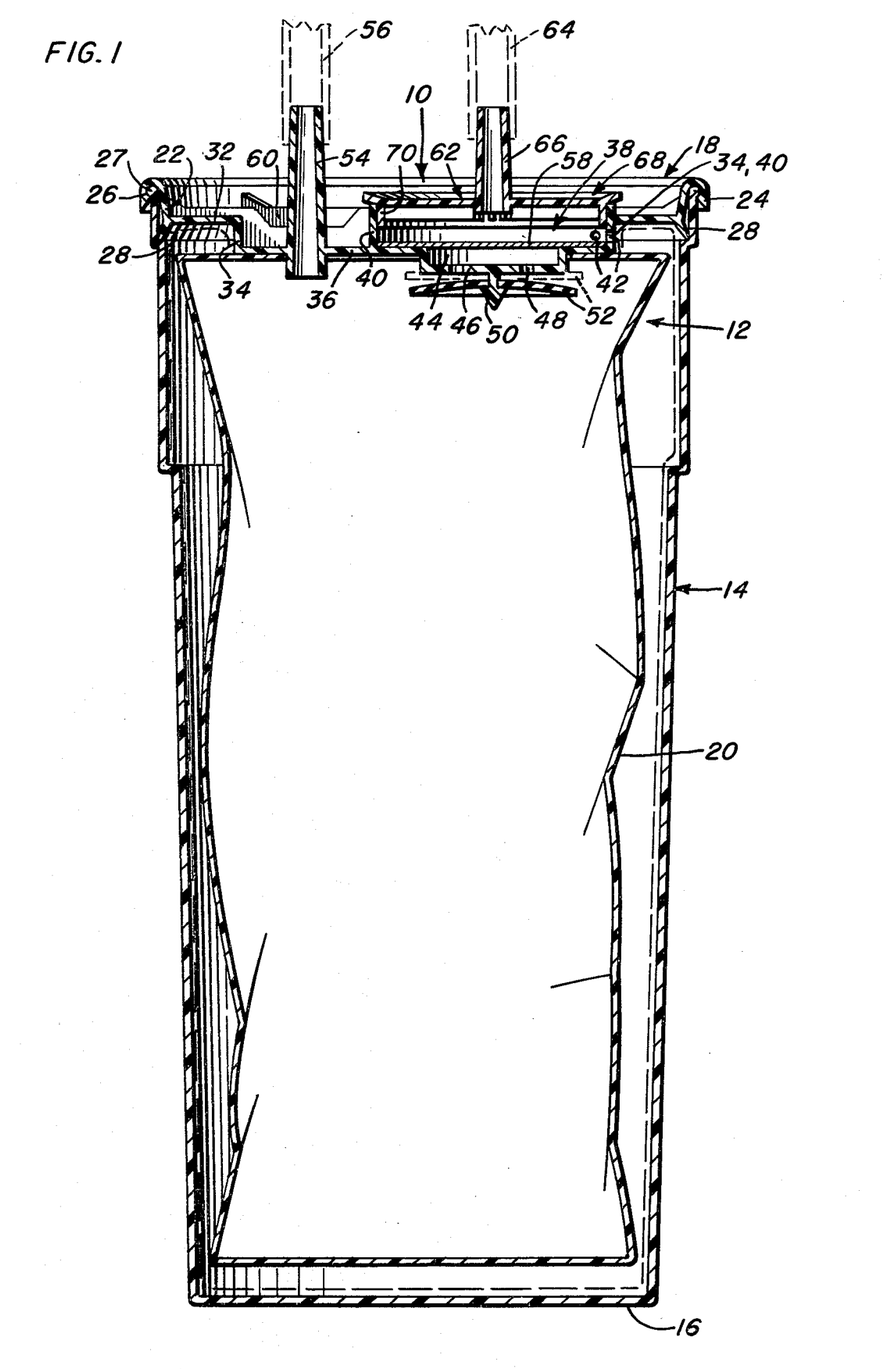
FIG. 1 is an enlarged vertical cross-sectional view through the suction collection system comprising the present invention.
Figure 2:
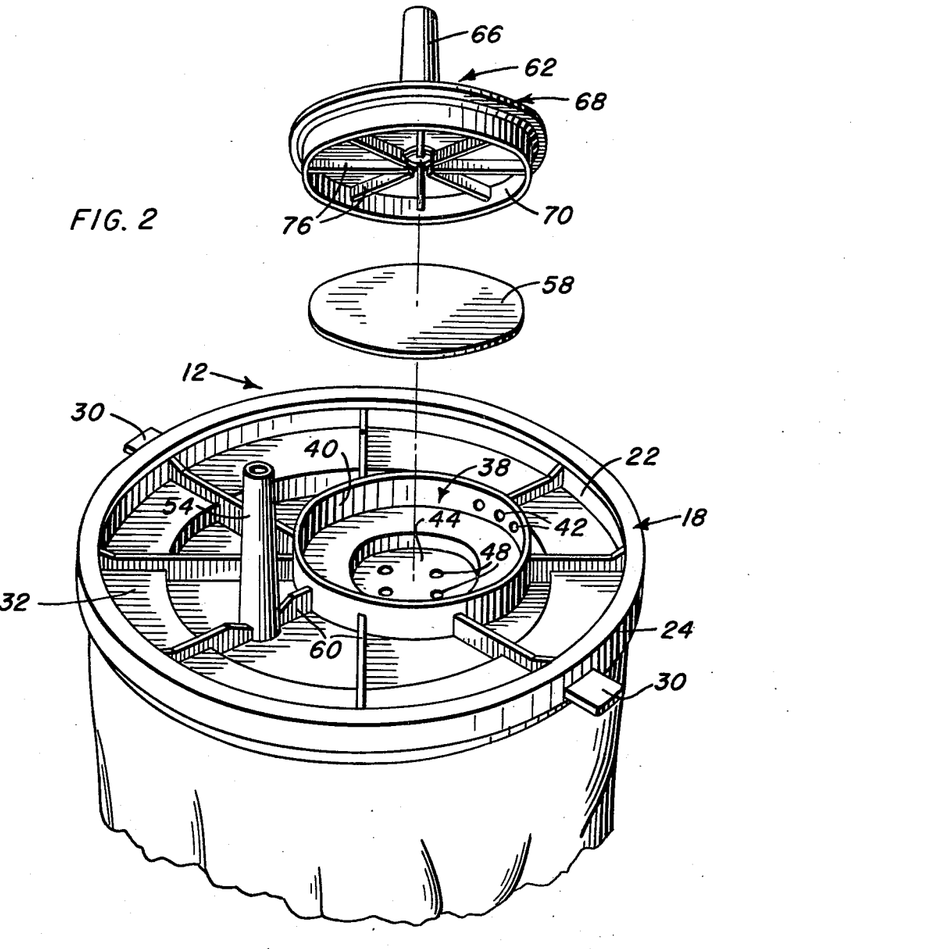
FIG. 2 is a top perspective view of the drainage receiving assembly with the suction line mounting fixture and the air pervious-fluid impervious patch exploded therefrom.
Figure 3:
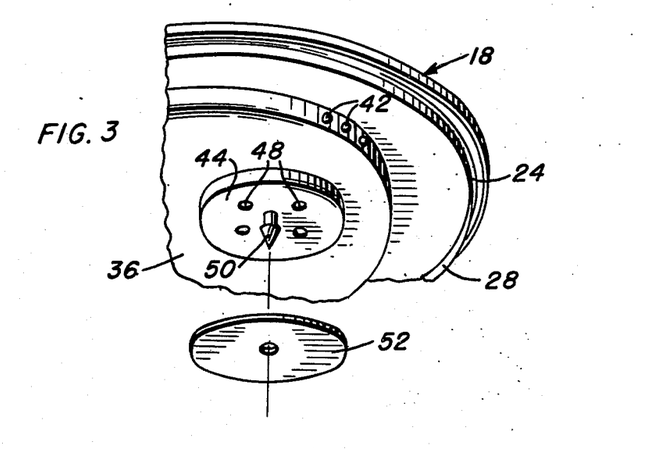
FIG. 3 is a fragmentary bottom perspective view of the lid with the disc seal exploded therefrom.

Referring now more specifically to the drawings, and FIGS. 1, 2 and 3 in particular, reference numeral 10 is used to generally designate a preferred embodiment of the suction collection system comprising the present invention. This system 10 utilizes a disposable drainage receiving assembly 12 received within a reusable rigid canister 14.

The canister 14 is both liquid and air impervious, and normally includes a closed flat base or lower end 16 and an open upper end for the selective reception of the drainage receiving assembly.

The drainage receiving assembly 12 includes a rigid lid 18 to which an elongated flexible air and water impervious bag of appropriate plastic material, such as polyethylene, is sealed as shall be described in more detail presently.

The lid 18 includes a peripheral upstanding wall 22, receivable immediately inward of the open end of the canister 14. The lid wall 22, at its upper end, is reversely bent outward and downward so as to define a depending flange 24 receivable immediately outward of the open end of the canister 14. The inner portion of the flange 24 is slightly undercut and, with the adjoining wall 22, defines a groove 26 which receives a bead 27 defined about the open upper end of the canister 14. By this means, provision is made for a snap locking and sealing of the lid 18 to the upper end of the canister with the flexible bag 20 therein as will be appreciated from the cross-sectional illustration of FIG. 1. A further sealing is effected by an integral annular flange 28 extending downwardly and outwardly below the wall 22 and inward of flange 24 for engagement with an annular shoulder defined within the upper portion of the canister 14 below the open end thereof. This flange 28, as will be noted, tapers to a thin sealing edge and may include a degree of resilient flexibility. Manipulation of the lid 14, and in particular the removal thereof, is facilitated by a pair of diametrically opposed extending tabs 30.

An annular shoulder 32 projects inwardly from the lower end of the peripheral wall 22, completely about the lid 18, and terminates in a depending inner wall 34 which surrounds the major depressed central portion 36.

A well-like compartment 38 is defined by a circular wall 40 rising vertically from the central portion 36 of the lid to a height slightly above the shoulder 32. The compartment 38 is diametrically smaller than the central portion 36 and orientated to one side thereof with the circular compartment wall 40 being integral and coextensive with a portion of the shoulder formed inner wall 34 along a section thereof. A set of apertures 42 extend through the coextensive portions of the walls 40 and 34 and communicates the interior of the canister 14 with the upwardly opening lid compartment 38.

The base of the compartment 38, defined by the depressed central portion 36 within the circular wall 40, is centrally recessed as at 44 with the circular base 46 of the recess having a plurality of apertures 48 at spaced points thereabout. An integral stem 50, headed on the lower end thereof, depends centrally from the base 46 and mounts an enlarged flat disc 52 of rubber or rubber-like material which provides a "float type" shut-off valve for the apertures 48. Upon the liquid level within the bag 20 rising to and above the level of the disc 52, the disc 52 will float upward and seal the apertures 48 to preclude the passage of liquid therethrough. As will be noted, the enlarged head of the stem 50 is in the shape of an inverted cone to facilitate a mounting of the disc 52 thereover.

A vertically elongated upwardly tapering hollow tubular fixture 54 is integrally formed with the center portion 36 outward of the wall 40 defining the compartment 38 and projects slightly below the central portion 36 and upwardly therefrom to a point substantially above the outer rim of the lid 18 for engagement of the discharge end of a drainage or inlet line 56 which will extend from the patient or source of fluid being collected.

The upper end of the flexible bag 20 is open with the peripheral edge sealed to the lower surface of the depressed central portion 36 immediately inward of the inner annular wall 34 and peripherally thereabout, enclosing the inner end of the drainage fixture 54 and the central apertured recess 44 of the compartment 38 with the subjacent stem supported disc 52, all of these elements and portions thus being located within the flexible bag 20. The set of apertures 42 communicates, as previously indicated, with the interior of the canister 14 exteriorly of the bag 20.

A circular disc or patch 58, of air pervious-liquid impervious material, overlies the base of the compartment 38, spanning the recess 44, and is sealed thereto inward of the circular wall 40 and outward of the recess 44, the patch 58 lying immediately below the set of apertures 42 communicating with the interior of the canister 14.

The lid 18 is rigidified, as is the circular wall 40, by a series of radially projecting raised ribs 60 which extend between the circular wall 40 and the outer wall 22, the ribs being integral with both the walls and the horizontal portions of the lid 18. As will be best appreciated from FIG. 2, one of the ribs 60 engages the drainage or inlet fixture 54 at diametrically opposed sides thereof, further stabilizing this member.

A second fixture 62 is provided in association with the compartment 38 and adapted to frictionally receive the end of the suction tube 64 which, as is conventional, extends to an appropriate vacuum or suction generating apparatus. The end of the tube 64 is frictionally engaged over the upper end of an elongated tubular member 66 projecting vertically and centrally from a circular cap 68. The cap 68 has a depending circular flange 70 which is frictionally received within the circular compartment wall 40 and provides a positive seal therewith, the lower edge of the flange terminating above the set of apertures 42. In order to facilitate a mounting of the cap 68, the upper edge 72 of the circular wall 40 is slightly inwardly beveled, defining in effect a wide mouth. A similar annular inclination is provided, at 74, on the undersurface of the top plate of the cap 68 immediately outward of the depending circular flange 70 so as to firmly and completely seat against the beveled edge 72. The flat top portion of the cap 68, noting FIG. 1, actually projects slightly beyond the compartment wall 40 peripherally thereabout. In addition, the cap 68 is internally rigidified by a plurality of radial ribs 76 which extends between the circular flange 70 and the inwardly projecting end of the tubular member 66. With the lower edge of flange 70 terminating above apertures 42, a clear air path is maintained between the hollow tubular member 66 and the canister interior through the apertures 42, while the air path between the tubular member 66 and the interior of the bag 20, though the apertures 48, is partially restricted by the air pervious-liquid impervious patch 58.

In use, the disposable drainage receiving assembly 12 is mounted within the canister 14 with the flexible bag 20 completely within the canister and the lid 18 sealed peripherally to the upper end of the canister 14. The drainage or inlet line 56 and the suction or outlet line 64 are then engaged with the respective fixtures or fixture members 54 and 66. FIG. 1 illustrates the bag 20, in full line, in its collapsed position as initially introduced into the canister 14. Upon activation of the vacuum or suction producing apparatus, air is evacuated from the lid compartment 38 and hence, through the communicating sets of apertures 42 and 48, from the canister outward of the bag 20 and from the interior of the bag 20. However, inasmuch as the patch 58 creates a slight resistance to air flow, a pressure differential will initially develop between the interior and exterior of the bag 20 which will evacuate the canister 14 exteriorly of the bag 20 prior to the development of the maximum vacuum within the bag 20. This in turn will result in an expansion of the bag 20, as illustrated in phantom lines in FIG. 1, to its full capacity, or the maximum volumetric capacity allowed by the interior of the canister 14.

Once the bag 20 has been fully expanded, drainage can commence by engaging the inlet or drainage line 56 with the source of fluid. It will be appreciated that the air pervious-liquid impervious patch 58 will preclude the passage of body fluids, foam emanating therefrom, or solids out of the sealed drainage receiving assembly. In this manner, contamination of the suction apparatus, the canister or the surrounding operative field is effectively precluded by means directly within the drainage receiving assembly itself. Should sufficient drainage occur so as to produce a liquid level, within the bag 20, which approaches the level of the apertures 48, the disc float 52 will rise and seal the apertures 48 to avoid any tendency for passage of liquid into the compartment recess 44, thus in effect providing a double seal, with the patch 58, against the outward discharge of any contaminants.

Upon a completion of the operation, or a filling of one bag 20, the lines 56 and 64 are disconnected and the entire drainage receiving assembly 12 removed and disposed of. As will be appreciated, the suction fixture 62, including the cap 68, can either remain with the suction tube 64 for reuse or can remain with the drainage receiving assembly 12 for disposal therewith. Also, appropriate means can be provided so as to cap the end of the inlet fixture 54 upon a disconnecting of the assembly.

Figure 4:
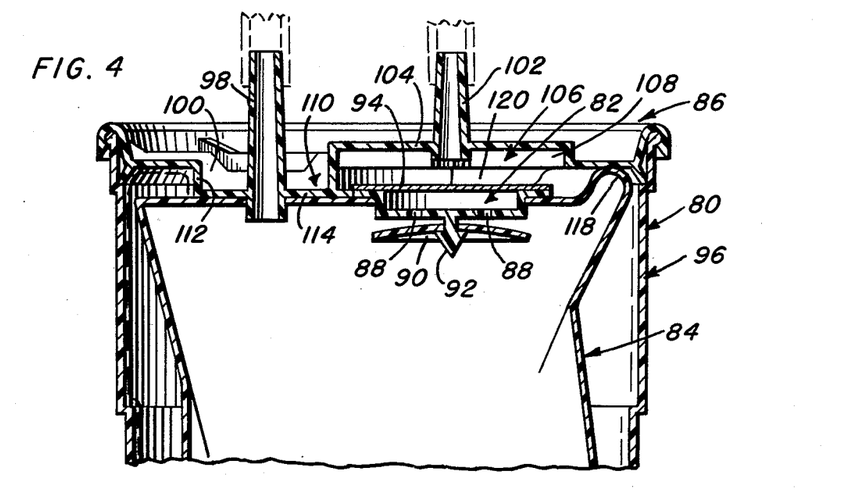
FIG. 4 is a partial vertical cross-sectional view through a suction collection system similar to that of FIG. 1.
Figure 5:
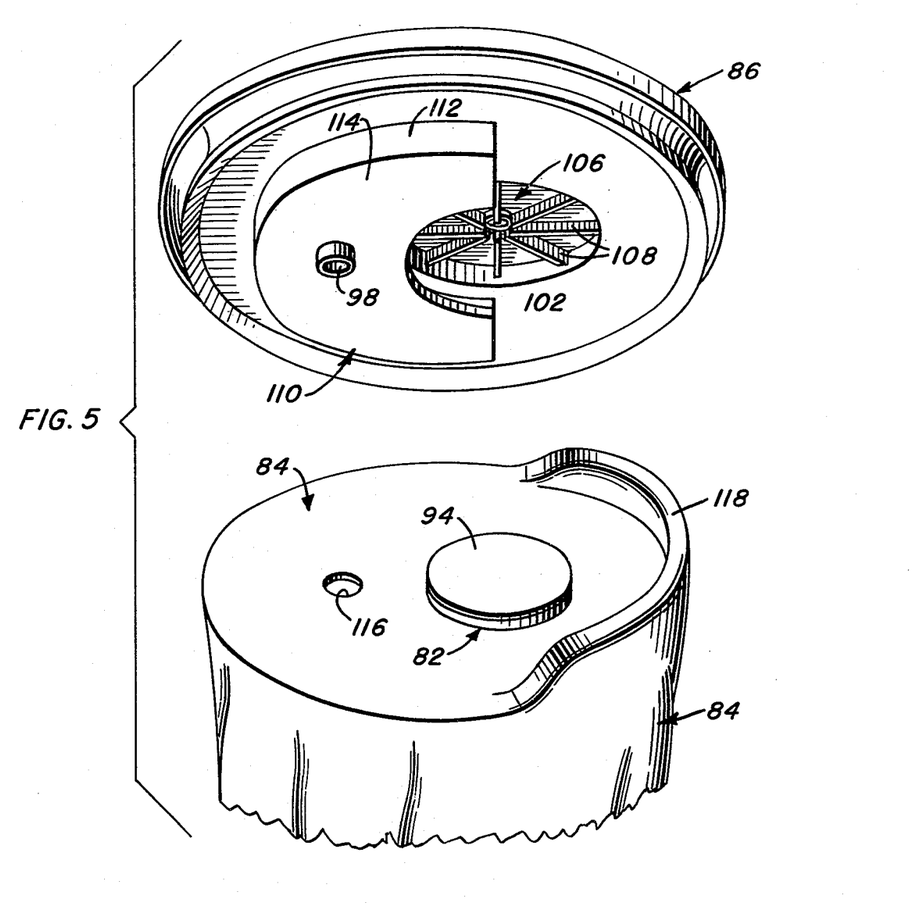
FIG. 5 is an exploded perspective view of the bag and lid of the system of FIG. 4.

Attention is now directed to FIGS. 4 and 5 wherein a variation of the suction collection system has been illustrated and designated by reference numeral 80. The system 80, while for the most part similar in construction and operation to the previously described system 10, differs therefrom in several particulars.

Specifically, the well or well-like compartment 82 is sealed directly to the bag 84, rather than to the lid 86. The compartment 82 projects through an opening in the bag 84 and communicates with the interior of the bag 84 through a series of apertures 88 which are selectively closed by the floating disc shut-off valve 90 mounted on the stem 92. The circular disc or patch 94, of air pervious-liquid impervious material, overlies the well compartment 82 and is sealed peripherally thereabout.

With regard to the lid 86, it will be noted that the releasable edge interlock with the canister 96 is the same as that previously described. In addition, the lid 86 includes the vertically extending drainage fixture 98 projecting both inwardly and outwardly therefrom, and the lid rididifying generally radially projecting ribs 100.

The lid 86 differs from the previously described lid in that the suction fixture is integrally formed therewith and includes the elongated tubular member 102 extending vertically and centrally from the elevated top wall 104 of a chamber 106 positioned so as to overlie the patch covered well compartment 82. Internal ribs 108, extending radially outward from the inwardly projecting end of the tubular member 102 to the surrounding wall can be provided if desired so as to both rigidify this portion of the lid and preclude any excessive upward drawing of the bag structure such as would tend to block the suction fixture.

The lid 86 also includes a recessed central portion 110, defined by a depending wall 112 and a bottom wall 114, which extends about approximately one half of the chamber 106. The drainage fixture 98 is mounted on and projects through the recessed bottom wall 110 and the bag 84 is sealed to the bottom wall 114 of the recess 110 peripherally about the inwardly projecting lower end of the drainage fixture 98. The bag aperture 116, which accommodates the fixture 98, will be noted in FIG. 5. The bag 84, to the opposite side of the well compartment 82 from the portion thereof sealed to the lid 86 about the drainage fixture 98, is upwardly folded, as at 118, and is also secured to the under surface of the lid 86. In this manner, the well compartment 82 is retained horizontally. The extent of the arcuate fold 118 which is secured or tacked to the under surface of the lid 86 can vary, but in all instances stops well short of the recessed portion 110 so as to retain a substantial passage, note 120 in FIG. 4, for the free flow of air between the suction fixture 102 and the interior of the canister 96 outward of the bag 84.

The manner of use and details of operation of the system 80 are the same as those set forth in connection with the described embodiment other than the obvious fact that the suction fixture, being an integral portion of the lid, must be disposed therewith.

Figure 6:
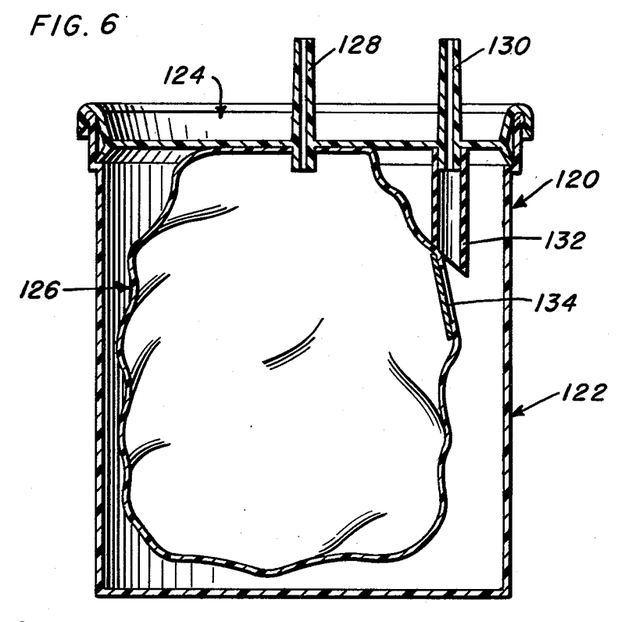
FIG. 6 is a vertical cross-sectional view through another related form of suction collection system.
Figure 7:
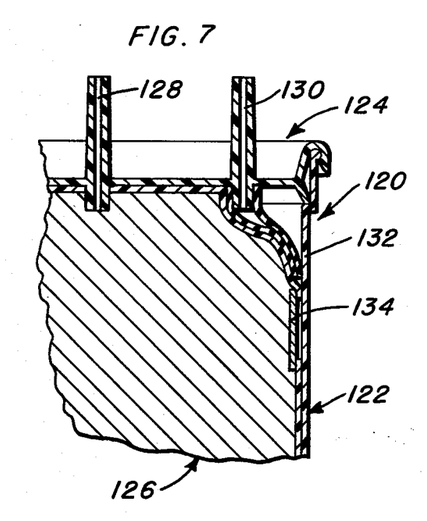
FIG. 7 is a partial cross-sectional view of the system of FIG. 6 illustrating a sealing off of the suction line.
Figure 8:
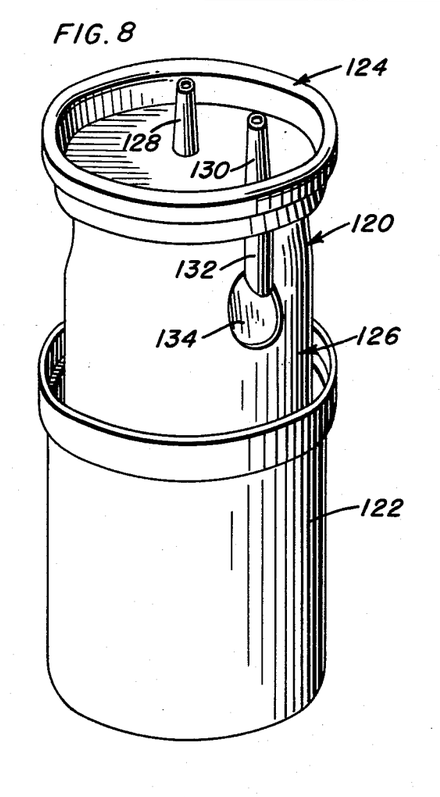
FIG. 8 is a perspective view of the system of FIG. 6 with the disposable drainage receiving assembly partially extracted from the canister.

Attention is now directed to FIGS. 6, 7 and 8 wherein another embodiment of the suction collection system has been illustrated. The embodiment herein is generally designated by reference numeral 120 and basically includes the rigid canister 122, the lid 124 which interlocks with the open upper end of the canister 122 in the same manner as with the previously described embodiments, and the expandable flexible bag 126 fixed to the under surface of the lid 124.

The drainage fixture 128 is in the nature of an elongated tubular member integral with and projecting centrally through the lid 124 with the projecting inner end of the fixture 128 communicating directly and solely with the interior of the bag 126 sealed thereabout.

The suction fixture 130 is also in the nature of an elongated tubular member integral with and projecting vertically through the lid 124 radially outward from the drainage fixture 128. The inwardly projecting end of the fixture 130 mounts an elongated collapsible elastomeric tube 132 through which the suction fixture is in direct communication with the interior of the canister 122 outward of the bag 126.

The necessary communication between the interior of the bag 126 and the suction fixture 130 is provided through a restricted fluid flow path defined in the side of the bag 126 by a circular disc or patch 134 of air pervious-liquid impervious material sealed directly to the bag about an opening defined therein. This patch is similar to the previously described patch, differing therefrom in that the patch 134 is directly sealed to the bag rather than associated with a bag or lid mounted well compartment.

The operation of the system 120 is basically similar to that previously described. The initial vacuum drawn through the suction fixture 130 will evacuate the canister 122 outward of the bag 126 so as to effect an expansion of the bag 126 with the relatively gentle pressure exerted by the expanding against the flexible tube 132 being insufficient so as to affect the exiting air flow therethrough particularly in view of the continuing although relatively restricted air flow through the patch 134. As a vacuum condition is generated within the bag 126, subsequent to a substantial evacuation of the canister 122 and the generation of a flow through the patch 134, the desired drainage through the drainage fixture and attached drainage line commences. This drainage will continue until such time as the liquid contents of the bag 126 forcibly expand the bag so as to physically compress and seal off the flexible tube 132. This situation has been illustrated in FIG. 7. It will also be noted that the patch 134 is positioned relatively high on the side of the bag 126. The patch itself performs a sealing function, being liquid impervious, and as such, as the liquid level within the bag 126 covers the patch 134, the restricted air flow path therethrough is shut off with the continued suction also tending to effect a collapse of the flexible tube 132. It is contemplated that both of these system sealing actions occur substantially simultaneously so as to combine to provide positive cutoff. The combined bag and lid can then be disposed of in any conventional manner.

From the foregoing, it will be appreciated that a unique suction collection system has been devised wherein the only hookup involved is the connection of the inlet and suction lines directly to the drainage receiving assembly which in turn snap locks within a rigid reusable canister. The pressure differential required so as to initially expand the flexible receiving bag for a proper drainage thereinto is achieved through operation of a single suction line by means of a formed compartment chambered by an air pervious-liquid impervious patch between two air flow paths respectfully communicating with the interior and exterior of the bag. This patch additionally, and importantly, functions so as to preclude the passage of contaminants. Also, within the disposable receiving assembly itself, a disc valve or seal provides for a positive cutoff of the suction upon the liquid reaching a predetermined level.

A variation of the above involves the mounting of the air pervious-liquid impervious patch directly on the bag, heat sealed thereto about an opening provided therein, with the suction fixture communicating with the interior of the canister exteriorly of the bag through a canister received collapsible rubber tube. The pressure differential developed by the air flow restricting nature of the patch will initially expand the bag and subsequently allow for a drainage of liquid into the bag until such time as an automatic cutoff is effected by the filling of the bag by the liquid.

All of the components, other than the flexible bag and the floating disc seal, are inexpensively formed of rigid molded plastic with the air and fluid flow controls, that is the patch and the seal, being portions of the disposable assembly whereby no possibility of contamination of any permanent component, such as the canister, is possible. Incidentally, it should be appreciated that the patch, orientated directly in the flow path, provides a further advantage in muffling the noise level of the suction equipment at the operating table.

The foregoing is illustrative only of the principles of the invention. Since modifications and changes may readily occur to those skilled in the art, it is not desired to limit the invention to the exact construction and operation shown and described. Accordingly, all suitable modifications and equivalents may be resorted to, falling within the scope of the invention as claimed.

What is claimed is:

1. For use in a collection system comprising a rigid reusable canister, a drainage receiving assembly, said drainage receiving assembly including a lid receivable over and releasably sealable to the canister, a drainage fixture fixed to and extending through said lid, a flexible receiving bag sealed to the lid about the drainage fixture and depending from said lid for reception within the canister, a suction fixture fixed to and extending through said lid in space relation to said drainage fixture, said suction fixture communicating with the exterior of said bag, an opening defined through said bag remote from said drainage fixture and communicating with the exterior of the bag and the suction fixture, and a patch of air pervious-liquid impervious material positioned directly over said bag opening between the bag and the suction fixture, and in the path of communication from the bag to the exterior of the bag inward of the canister and inward of the suction fixture.

2. A suction collection system comprising a canister having an open end, a lid received over the open end of the canister and releasably sealed to the canister, a flexible receiving bag sealed to the lid and depending therefrom for reception within the canister, said lid and said bag being configured to define a flow accommodating compartment therein and therebetween, said compartment being at least partially closed and having first fluid path means therefrom communicating solely with the interior of the bag and second fluid path means therefrom communicating solely with the interior of the canister exteriorly of the bag, an air pervious-liquid impervious patch positioned in said compartment and solely overlying said first fluid path means between the first and second fluid path means, a suction outlet fixture in communication with said compartment for the mounting of a suction line in sealed relation to the compartment outward of the second fluid path means for the drawing of a vacuum through both the patch overlying first fluid path means and second fluid path means, said patch creating a resistance to air flow from the interior of the bag through the first fluid path means as opposed to the air flow through the second fluid path means to effect an initial expansion of the flexible bag upon the exhausting of air through the suction line, and a fluid inlet fixture on said lid in communication with the interior of the bag for mounting a fluid inlet line.

3. The system of claim 2 including a float valve mounted below said first fluid path means within said bag for a selective vertical movement thereof into sealing engagement with said first fluid path means in response to a rising liquid level.

4. The system of claim 3 wherein said compartment includes a base integral with the lid, a peripheral wall surrounding said base, and a recess in said base, said first fluid path means comprising first aperture means defined in said recess, said second fluid path means comprising second aperture means defined through said peripheral wall above said recess, and said patch being fixed in overlying relation to said recess below said second aperture means.

5. The system of claim 4 wherein said recess includes a flat bottom, said first aperture means being defined through said flat bottom, a vertically elongated stem fixed to the exterior of said flat bottom and depending therefrom, said float valve being slidably mounted on said stem.

6. The system of claim 5 wherein said suction outlet fitting comprises a cap overlying the upper edge of the peripheral wall of the compartment, said cap having a depending peripheral flange frictionally received within said peripheral wall, and an upwardly projecting tubular memeber fixed to said cap for the frictional reception of a suction line.

7. The system of claim 6 wherein said peripheral flange terminates above said second aperture means within said compartment.

8. The system of claim 7 wherein the upper edge of the peripheral wall is inwardly beveled, said cap immediately outward of the peripheral flange, including an inclined annular portion mating with the beveled wall edge.

9. The system of claim 8 including rigidifying ribs on said cap extending inwardly from said peripheral flange at spaced points thereabout.

10. The system of claim 9 including rigidifying ribs on said lid extending generally radially, outward from the peripheral wall of the compartment, at spaced points thereabout.

11. The system of claim 2 wherein said fluid inlet fitting is positioned outward of said compartment.

12. The system of claim 2 wherein said compartment includes a central well with a closed bottom, a peripheral wall about at least a portion of the well, said first fluid path means being defined through bottom of the well, said second fluid path means being defined through said peripheral wall above said well bottom, and said patch being fixed in spanning relation to said well below said second fluid path means.

13. The system of claim 2 wherein said compartment includes a well fixed to said bag below said lid and a chamber integrally formed in said lid above said well, said patch being fixed to said bag in overlying relation to said well.

14. The system of claim 13 wherein said bag includes a first portion thereof sealed to said lid about said inlet fixture and a second portion thereof secured to said lid, in spaced relation to said first portion, to the opposite side of the lid chamber from said inlet fixture.

15. The system of claim 14 wherein said first fluid path means is defined through said well, said second fluid path means being defined between said bag and said lid in the area between the first and second lid engaged portions of the bag.

16. For use in a collection system including a rigid reusable canister, a drainage receiving assembly, said drainage receiving assembly comprising a rigid canister sealing lid, a flexible bag sealed to said lid and depending therefrom for reception within the canister, a first air flow path defined through said lid and in communication with the interior of said bag, a second air flow path defined through said lid and communicating with the exterior of the bag immediately adjacent thereto for communication with the interior of the canister upon a mounting of the lid thereon, means on said lid, outward of both air flow paths, for mounting a single suction line in communication with both air flow paths, and an air pervious-liquid impervious member solely within said air flow path for a control of flow in said first air path independent of flow in said second air path.

17. The assembly of claim 16 including float valve means mounted on said lid within said bag and selectively movable into sealing relation solely with said first air flow path and independent of said second air flow path.

18. For use in a collection system comprising a rigid reusable canister, a drainage receiving assembly including a lid receivable over and releasably sealable to the canister, a flexible receiving bag sealed to the lid and depending therefrom for reception within the canister, a separate compartment defined generally between said lid and said bag, said compartment having first fluid path means therefrom communicating solely with the interior of the bag and second fluid path means therefrom opening through the lid and to the exterior of the bag immediately adjacent thereto, an air pervious-liquid impervious member positioned in said compartment and solely overlying said first fluid path means between said first and second fluid path means, and means for mounting a suction outlet fitting in communication with said compartment outward of said air pervious-liquid impervious member to effect a restricted drawing of air through the first fluid path means and overlying air pervious-liquid impervious member, and an unrestricted drawing of air through said second fluid path means.

19. The assembly of claim 18 wherein said compartment includes a base, a peripheral wall surrounding said base and rising therefrom, and a recess in said base, said first fluid path means being defined through said recess, said second fluid path means being defined through said peripheral wall above said recess, a air pervious-liquid impervious member being fixed in overlying relation to said recess below said second fluid path means.

20. The assembly of claim 18 wherein said compartment includes a well fixed to said bag below said lid and a chamber integrally formed in said lid above said well, said patch being fixed to said bag in overlying relation to said well.

21. The assembly of claim 20 wherein said bag includes a first portion thereof sealed to said lid about said inlet fixture and a second portion thereof secured to said lid, in spaced relation to said first portion, to the opposite side of the lid chamber from said inlet fixture.

22. For use in a collection system comprising an upwardly opening rigid reusable canister, a drainage receiving assembly, said drainage receiving assembly including a lid receivable over and releasably sealable to the canister, said lid including a drainage fixture fixed thereto and opening therethrough, a flexible fluid receiving bag sealed to the lid in surrounding relation to said drainage fixture, said bag depending from said lid for reception within the canister, said drainage fixture communicating solely with the interior of the bag, said lid further including a suction fixture fixed thereto and extending therethrough, said suction fixture being orientated outward of the portion of the bag sealed to the lid and out of communication with the interior of the bag for direct communication with the interior of the canister exteriorly of the bag upon a mounting of the drainage receiving assembly to the canister, an opening defined through said bag toward the upper portion thereof and below the lid, and a patch of air pervious-liquid impervious material overlying said opening and sealed to the bag thereabout for allowing a suction generated restrictive air flow therethrough.

23. The assembly of claim 22 including a collapsible tube depending from the suction fixture immediately adjacent the exterior of the bag for a selective collapsing and sealing thereof upon an expansion of the bag.

* * * * *

REEXAMINATION CERTIFICATE (44th)

United States Patent [19]
Hessel

[11] B1 4,111,204
[45] Certificate Issued Jan. 18, 1983

[54] SUCTION COLLECTION SYSTEM

[75] Inventor: Stephen Roy Hessel, Somerville, N.J.

[73] Assignee: C. R. Bard, Inc., Murray Hill, N.J.

Reexamination Request
No. 90/000,168, Feb. 25, 1982

Reexamination Certificate for:
Patent No.: 4,111,204
Issued: Sep. 5, 1978
Appl. No.: 730,404
Filed: Oct. 7, 1976

[51] Int. Cl.³ .............................................. A61M 1/00
[52] U.S. Cl. ...................................................... 128/276
[58] Field of Search .......... 128/275–278, 283; 137/137, 137/202, 205; 15/351, 353; 73/322.5

[56] References Cited

U.S. PATENT DOCUMENTS

| | | | |
|---|---|---|---|
| 3,680,560 | 8/1972 | Pannier et al. | 128/276 |
| 3,768,478 | 10/1973 | Fertik | 128/276 |
| 3,719,197 | 3/1973 | Pannier et al. | 137/205 |
| 3,811,485 | 5/1974 | Holbrook | 141/59 |

Primary Examiner—V. Millin

[57] ABSTRACT

A suction collection system embodying a disposable drainage receiving assembly including a flexible plastic bag sealed to and depending from a lid for positioning within a rigid canister, the open upper end of the canister being sealed by the lid. The lid includes a drainage fixture communicating with the interior of the bag. A suction fixture, also on the lid, communicates with the canister exteriorly of the bag and with the interior of the bag through a restricted fluid path. The suction fixture communication with the canister exteriorly of the bag can be either direct or through a well having a fluid path to the exterior of the bag and a set of apertures opening into the bag. An air pervious-liquid impervious path is orientated solely between the suction fixture and the interior of the bag for an exclusion of liquid and a slight restriction of air flow relative to the flow from the canister exteriorly of the bag. A seal, either a liquid level responsive disc or a compressible tube, will, upon the introduction of a sufficient level of liquid within the bag, terminate communication between the suction fixture and the interior of the bag.

REEXAMINATION CERTIFICATE ISSUED UNDER 35 U.S.C. 307.

NO AMENDMENTS HAVE BEEN MADE TO THE PATENT.

AS A RESULT OF REEXAMINATION, IT HAS BEEN DETERMINED THAT:

The patentability of claims 1–23 is confirmed.

* * * * *